(12) United States Patent
Walsh (10) Patent No.: US 8,613,694 B2
(45) Date of Patent: Dec. 24, 2013

(54) METHOD FOR BIOLOGICAL MODULATION OF RADIATION THERAPY

(76) Inventor: James Sherman Walsh, Shreveport, LA (US)

( * ) Notice: Subject to any disclaimer, the term of this patent is extended or adjusted under 35 U.S.C. 154(b) by 328 days.

(21) Appl. No.: 13/010,047

(22) Filed: Jan. 20, 2011

(65) Prior Publication Data

US 2011/0180731 A1 Jul. 28, 2011

(51) Int. Cl.
*A61N 5/00* (2006.01)

(52) U.S. Cl.
USPC .................................. 600/1; 378/65

(58) Field of Classification Search
USPC ............................ 600/1–2; 378/64–65, 68–69
See application file for complete search history.

(56) References Cited

U.S. PATENT DOCUMENTS

| | | | |
|---|---|---|---|
| 4,870,287 A | 9/1989 | Cole et al. | |
| 5,084,001 A * | 1/1992 | Van't Hooft et al. | 600/3 |
| 5,341,292 A | 8/1994 | Zamenhof | |
| 5,661,773 A | 8/1997 | Swerdloff et al. | |
| 2004/0165696 A1* | 8/2004 | Lee | 378/65 |

FOREIGN PATENT DOCUMENTS

| | | | |
|---|---|---|---|
| WO | 2006018761 A1 | | 2/2006 |
| WO | WO 2006/018761 | * | 2/2006 |

OTHER PUBLICATIONS

Welsh, et al., Dose-rate Radiobiology of Large Fractions, Proceedings of the Second Annual Extracranial Stereotactic Radioablation, May 2003, 2 pages.
Bortfeld et al., Realization and Verification of Three-Dimensional Conformal Radiotherapy With Modulated Fields, Int. J. Radiation Oncology Biol. Phys., 1994, 30:899-908.
Carol et al., The Field-Matching Problem as it Applies to the Peacock Three Dimensional Conformal System for Intensity Modulation, Int. J. Radiation Oncology Biol. Phys., 1996; 34:183-187.
Fowler et al., Loss of Biological Effect in Prolonged Fraction Delivery, Int. J. Radiation Oncology Biol. Phys., 2004; 59:242-249.
Richards, et al., Pulsed Reduced Dose-Rate Radiotherapy: A Novel Locoregional Retreatment Strategy for Breast Cancer Recurrence in the Previously Irradiated Chest Wall, Axilla, or Supraclavicular Region, Breast Cancer Res. Treat. 2008, 7 pages.
Tome, et al., The Effect of Fraction Time in Intensity Modulated Radiotherapy: Theoretical and Experimental Evaluation of an Optimization Problem (The Real Conclusions), Radiotherapy and Oncology, 2004, 72(1):113-114.
Welsh, et al., Radiation Dose-rate Considerations with Intensity Modulated Radiation Therapy, Radiotherapy and Oncology, 2002, 64(Suppl 1):S312.
Welsh, et al., Dose Rate in External Beam Radiotherapy for Prostate Cancer: An Overlooked Confounding Variable?, Urology, 2003, 62(2):204-206.

(Continued)

*Primary Examiner* — Charles A Marmor, II
*Assistant Examiner* — Laura Fajardo
(74) *Attorney, Agent, or Firm* — Quarles & Brady, LLP (57) ABSTRACT

A method for the biological modulation of external beam radiation therapy, in which the temporal and spatial patterning of imparted dose is modified to maximize the dose rate to the target volume while minimizing the dose rate to healthy tissues surrounding the target volume, is provided.

16 Claims, 5 Drawing Sheets

(56) References Cited

OTHER PUBLICATIONS

Chau, et al., A Split-organ Delineation Approach for Dose Optimisation for Intensity-modulated Radiotherapy for Advanced T-stage Nasopharyngeal Carcinoma, Clinical Oncology, 2008, 20:134-141.*

Welsh, et al., Dose-rate in IMRT: An Overlooked Confounding Variable?, P025, Cancer Journal, 2003, 9(6):508.

Welsh, et al., Reduced Toxicity Re-irradiation Techniques: Pulsed Low-dose-rate and Grid External Beam Radiation Therapy, RSNA Radiology's Global Forum, 2004, Abstract Only.

Xia et al., Multileaf Collimator Leaf Sequencing Algorithm for Intensity Modulated Beams with Multiple Static Segments, Medical Physics, 1998; 25:1424-1434.

Yu, Intensity-Modulated Arc Therapy With Dynamic Multileaf Collimation: An Alternative to Tomotherapy, Physics in Medicine & Biology, 1995; 40:1435-1449.

PCT International Search Report and Written Opinion, PCT/US2011/021805, Apr. 21, 2011.

* cited by examiner

METHOD FOR BIOLOGICAL MODULATION OF RADIATION THERAPY

CROSS-REFERENCE TO RELATED APPLICATIONS

This application claims the benefit of, and herein incorporates by reference in its entirety, U.S. Provisional Patent Application Ser. No. 61/298,040, filed on Jan. 25, 2010, and entitled "Method for Biological Modulation of Radiation Therapy."

BACKGROUND OF THE INVENTION

The field of the invention is radiation therapy systems and methods. More particularly, the invention relates to systems and methods for radiobiological effect modulated external beam radiation therapy.

Radiation therapy is a treatment technique that delivers ionizing radiation to a defined target volume in a patient. Preferably, the radiation is delivered in such a manner that the surrounding healthy tissue does not receive radiation doses in excess of clinically acceptable tolerances. In order to achieve this control of the imparted dose to the subject, highly accurate radiation delivery techniques are required. Many factors provide difficulties in obtaining the desired level of accuracy, including differences between the planned and delivered dose distributions and uncertainty in subject position with respect to the treatment system.

Conventional external beam radiation therapy, also referred to as "teletherapy," is commonly administered by directing a linear accelerator ("linac"), or cobalt-60 teletherapy unit, to produce beams of ionizing radiation that irradiate the defined target volume in a patient. The radiation beam is a single beam of radiation that is delivered to the target region from several different directions, or beam paths. Together, the determination of how much dose to deliver along each of these beam paths constitutes the so-called radiation therapy "plan." The purpose of the treatment plan is to accurately identify and localize the target volume in the patient that is to be treated. This technique is well established and is generally quick and reliable.

Intensity modulated radiation therapy ("IMRT") is an external beam radiation therapy technique that utilizes computer planning software to produce a three-dimensional radiation dose map, specific to a target tumor's shape, location, and motion characteristics. Various regions within a tumor and within the patient's overall anatomy may receive varying radiation dose intensities through IMRT, which treats a patient with multiple rays of radiation, each of which may be independently controlled in intensity and energy. Each of these rays or beams is composed of a number of sub-beams or beamlets, which may vary in their individual intensity, thereby providing the overall intensity modulation. Because of the high level of precision required for IMRT methods, detailed data must be gathered about tumor locations and their motion characteristics. In doing so, the radiation dose imparted to healthy tissue can be reduced while the dose imparted to the affected region, such as a tumor, can be increased. In order to achieve this, accurate geometric precision is required during the treatment planning stage. Thus, while conventional IMRT methods have had success in increasing the physical dose imparted to the defined target volume while mitigating the imparted radiation dose to the surrounding healthy tissue, further reduction of the radiobiological effect on healthy tissue is desirable. Particularly, while IMRT has effectively reduced the physical absorbed dose of radiation to sensitive areas within a patient, there is still room for improvement in reducing the biological effect of such radiation.

In general, methods of producing intensity modulated rays of radiation are well known in the art. Exemplary methods include (1) stop and shoot methods, such as the one described by P. Xia and L. J. Verhey in "Multileaf Collimation Leaf Sequencing Algorithm for Intensity Modulated Beams with Multiple Static Segments," *Medical Physics*, 1998; 25:1424-1434; (2) sliding window methods, such as the one described by T. Bortfeld, et al., in "Realization and Verification of Three-Dimensional Conformal Radiotherapy With Modulated Fields," *Int'l J. Radiat. OncoL Biol. Phys.*, 1994; 30:899-908; (3) intensity modulated arc therapy methods, such as the one described by C. X. Yu in "Intensity-Modulated Arc Therapy With Dynamic Multileaf Collimation: An Alternative to Tomotherapy," *Physics in Medicine & Biology*, 1995; 40:1435-1449; and (4) sequential (axial) tomotherapy methods, such as the one described by M. Carol, et al., in "The Field-Matching Problem as it Applies to the Peacock Three Dimensional Conformal System for Intensity Modulation," *Int'l J. Radiat. Oncol. Biol. Phys.*, 1996; 34:183-187.

Image-guided radiation therapy ("IGRT") employs medical imaging, such as computed tomography ("CT"), concurrently with the delivery of radiation to a subject undergoing treatment. In general, IGRT is employed to accurately direct radiation therapy using positional information from the medical images to supplement a prescribed radiation delivery plan. The advantage of using IGRT is twofold. First, it provides a means for improved accuracy of the radiation field placement. Second, it provides a method for reducing the dose imparted to healthy tissue during treatment. Moreover, the improved accuracy in the delivery of the radiation field allows for dose escalation in the tumor, while mitigating dose levels in the surrounding healthy tissue. The concern remains, however, that some high-dose treatments may be limited by the radiation tolerance of healthy tissues that lay close to the target tumor volume.

It would therefore be desirable to provide a method for performing external beam radiation therapy that permits high levels of dose to a target volume of interest while further controlling damage to healthy tissue and organs at risk surrounding the target volume being treated.

SUMMARY OF THE INVENTION

The present invention overcomes the aforementioned drawbacks by providing a method for the biological modulation of external beam radiation therapy, in which the temporal and spatial patterning of imparted dose is modified to maximize the dose rate to the target volume, while minimizing the dose rate to healthy tissues surrounding the target volume.

It is an aspect of the invention to provide a method for reducing the biological effect on normal tissues surrounding a planned target volume ("PTV") by lowering the effective dose rate experienced by those tissues while maintaining a clinically significant effective dose rate in the PTV. Through the provided method, the total prescribed dose delivered to the PTV can be increased without negative side effects on the normal tissues surrounding the PTV. In this manner, the cancer cure rate can be increased because the total dose to the cancer is greater, while the surrounding healthy tissues and organs at risk can be spared.

It is another aspect of the invention to provide a method for determining the spatiotemporal patterns for intra-fraction radiation dose delivery rate in external beam radiation therapy that further reduce the radiobiological effect on normal tissue over traditional methods, while maintaining clinically significant dose rate in a PTV.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

The succeeding description of the invention is made with respect to an idealized, exemplary image-guided radiation therapy ("IGRT") system; however, it should be readily appreciated by those skilled in the art that the invention can additionally be practiced in any number of radiation therapy systems. For example, stereotactic radiosurgery systems such as the CyberKnife® system (Accuray, Sunnyvale, California), traditional gantry-mounted linear accelerator ("linac") systems, and cobalt-60 teletherapy systems can be readily employed. Additionally, hadron therapy systems, such as proton beam therapy systems and heavy ion beam therapy systems, may be employed when practicing the invention. It will also be appreciated by those skilled in the art that in addition to therapeutic x-rays, IGRT and intensity modulated radiation therapy ("IMRT") systems may use gamma rays produced, for example, by a cobalt-60 radiation source to deliver therapeutic radiation to a patient.

Figure 1:
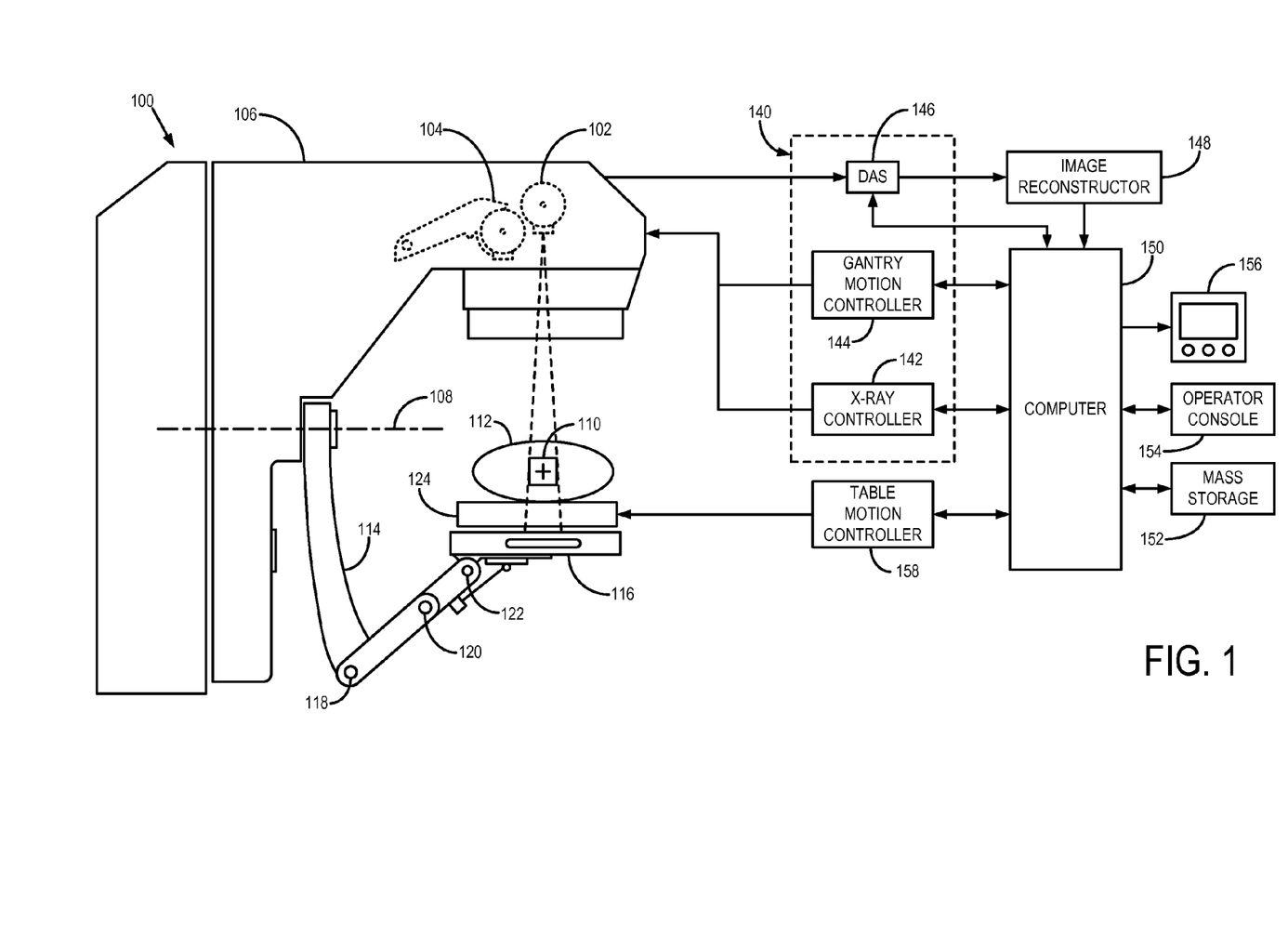
FIG. 1 is a block diagram of an exemplary image-guided radiation therapy ("IGRT") system.

Referring to FIG. 1, an exemplary image-guided radiation therapy ("IGRT") system 100 includes a therapeutic x-ray source 102 and a diagnostic x-ray source 104. The diagnostic x-ray source 104 projects a cone-beam of x-rays toward a detector array 116. Both the therapeutic x-ray source 102 and diagnostic x-ray source 104 are attached adjacent each other and housed at the same end of a first rotatable gantry 106, which rotates about a pivot axis 108. The first rotatable gantry 106 allows either of the x-ray sources, 102 and 104, to be aligned in a desired manner with respect to a target volume 110 in a subject 112 positioned on a patient table 124. A second rotatable gantry 114 is rotatably attached to the first rotatable gantry 106 such that it too is able to rotate about the pivot axis, 108. Disposed on one end of the second rotatable gantry 114 is an x-ray detector 116. The x-ray detector 116 functions not only as a diagnostic image device when receiving x-rays from the diagnostic x-ray source 104, but also as a portal image device when receiving x-rays from the therapeutic x-ray source 102. The detector array 116 is formed by a number of detector elements that together sense the projected x-rays that pass through the subject 112. Each detector element produces an electrical signal that represents the intensity of an impinging x-ray beam and, hence, the attenuation of the beam as it passes through the subject 112. The second rotatable gantry 114 further includes an articulating end that can pivot about three points 118, 120, and 122. The pivoting motion provided by these points 118, 120, and 122, allows the x-ray detector 116 to be moved within a two-dimensional plane.

The rotation of the rotatable gantries, 106 and 114, and the operation of the x-ray sources, 102 and 104, are governed by a control mechanism 140 of the IGRT system. The control mechanism 140 includes an x-ray controller 142 that provides power and timing signals to the x-ray sources, 102 and 104, and a gantry motor controller 144 that controls the rotational speed and position of the gantries, 106 and 114. A data acquisition system ("DAS") 146 in the control mechanism 140 samples analog data from detector elements and converts the data to digital signals for subsequent processing. An image reconstructor 148, receives sampled and digitized x-ray data from the DAS 146 and performs high speed image reconstruction. The reconstructed image is applied as an input to a computer 150 which stores the image in a mass storage device 152.

The computer 150 also receives commands and scanning parameters from an operator via a console 154 that has a keyboard. An associated display 156 allows the operator to observe the reconstructed image and other data from the computer 150. The operator supplied commands and parameters are used by the computer 150 to provide control signals and information to the DAS 146, the x-ray controller 142 and the gantry motor controller 144. In addition, the computer 150 operates a table motor controller 158 which controls the motorized patient table 124 to position the subject 112 within the gantries, 106 and 114.

Figure 2:
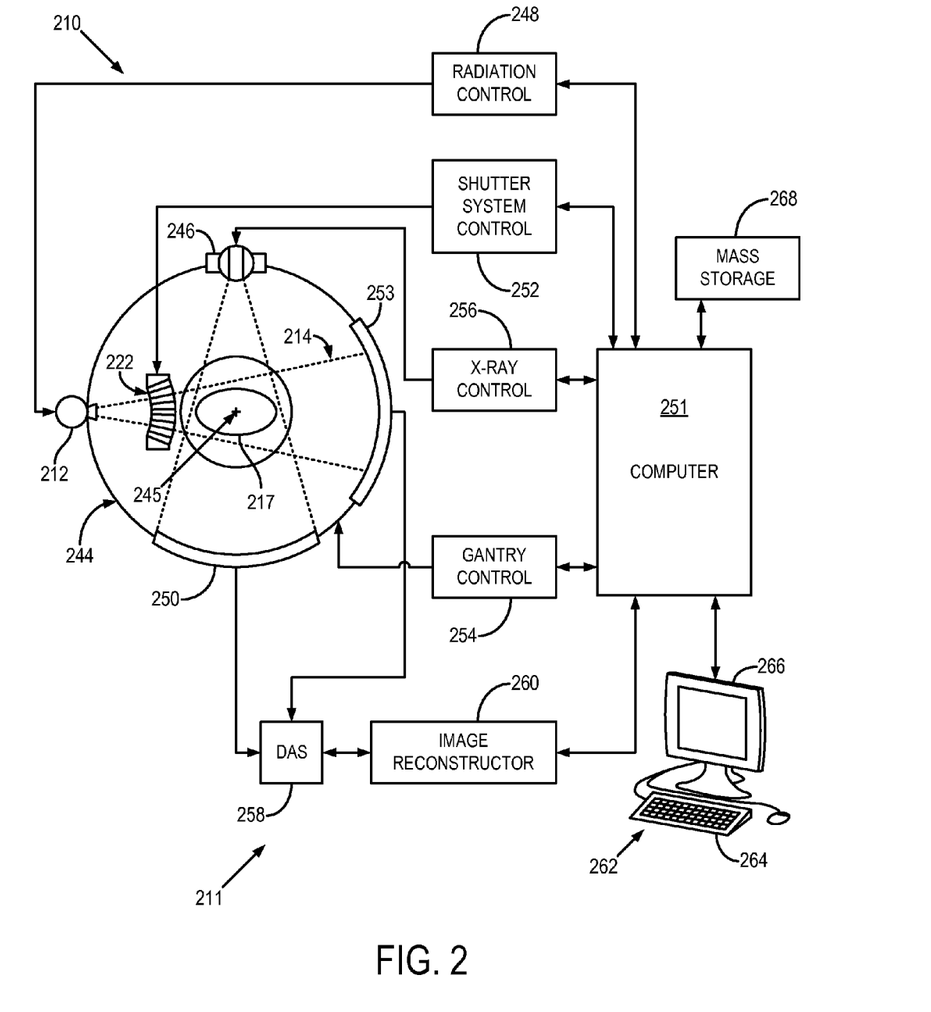
FIG. 2 is a block diagram showing the elements of a radiation therapy system incorporating a conventional computed tomography ("CT") system and including a computer suitable for controlling the radiation therapy system.

Referring now to FIG. 2, an exemplary tomotherapy IGRT system 210 includes a radiation source 212 producing a generally conical radiation beam, or "field," 214 emanating from a focal spot and directed toward a patient 217. The conical radiation beam 214 is collimated by a rectangular opaque mask (not shown) constructed of a set of rectangular shutter system blades to form a generally planar radiation fan beam 214 centered about a radiation fan beam plane.

A shutter system 222 is centered in the radiation fan beam 214 and about the radiation fan beam plane prior to the radiation beam being received by the patient 217, and includes a plurality of adjacent trapezoidal leaves which together form an arc of constant radius about the focal spot. Each leaf is constructed of a dense radio-opaque material such as lead, tungsten, cerium, tantalum, or related alloy.

The radiation source 212 is mounted on a gantry 244, the latter rotating within the radiation fan beam plane about a center of rotation 245 in the patient 217 so that the radiation fan beam 214 may irradiate a slice of the patient 217 from a variety of gantry angles, θ. The radiation source 212 is controlled by a radiation control module 248 which turns the radiation beam 214 on or off under the control of a computer 251.

A shutter system control 252 directed by a timer generating desired position signals provides electrical excitation to each electromagnet to control, separately, actuators to move each of the leaves in and out of its corresponding sleeve and ray. The shutter system control 252 moves the leaves of the shutter system 222 rapidly between their open and closed states to either fully attenuate or provide no attenuation to each ray. Gradations in the fluence of each ray, as needed for the fluence profile, are obtained by adjusting the relative duration during which each leaf is in the closed position compared to the relative duration during which each leaf is in the open position for each gantry angle.

The ratio between the closed and open states or the "duty cycle" for each leaf affects the total energy passed by a given leaf at each gantry angle, θ, and thus controls the average fluence of each ray. The ability to control the average fluence at each gantry angle, θ, permits accurate control of the dose provided by the radiation beam 214 through the irradiated volume of the patient 217 by therapy planning methods to be described below. The shutter system control 252 also connects with computer 251 to allow program control of the shutter system 222 to be described.

An optional tomographic imaging system 211 employing an x-ray source 246 and an opposed detector array 250 may be advantageously mounted on the same gantry 244 as the radiation source 212 to produce a tomographic or slice image of the irradiated slice of the patient 217 prior to radiation therapy for planning purposes or during treatment. Alternatively, such tomographic imaging may be performed on a separate machine and the slices aligned according to fiducial points on the patient 217.

A gantry control module 254 provides the signals necessary to rotate the gantry 244 and hence to change the position of the radiation source 212 and the gantry angle, θ, of the radiation fan beam 214 for the radiation therapy, as well as for the computer tomography x-ray source 246 and detector array 250, also attached to gantry 244. Gantry control module 254 connects with computer 251 so that the gantry may be rotated under computer control and also to provide the computer 251 with a signal indicating the gantry angle, θ, to assist in that control.

Control modules for the tomographic imaging system 211 include an x-ray control module 256 for turning on and off the x-ray source 246, and a data acquisition system 258 for receiving data from the detector array 250 in order to construct a topographic image.

An image reconstructor 260, typically including a high speed array processor or the like, receives the data from the data acquisition system 258 in order to assist in "reconstructing" a tomographic treatment image from such acquired image data according to methods well known in the art. The image reconstructor 260 may also use post-patient radiation detector signals from the radiation detector 253 to produce a tomographic absorption image to be used for verification and future therapy planning purposes as described in more detail below.

A computer terminal 262 including a keyboard 264 and display unit 266 allows an operator to input programs and data to the computer 251; control the radiation therapy system 210 and the tomographic imaging system 211; and to display images provided by the image reconstructor 260 on display unit 266.

A mass storage system 268, being, for example, a magnetic disk unit or tape drive, allows the storage of data collected by the tomographic imaging system 211 and the post-patient radiation detector 253 for later use. Computer programs for operating the radiation therapy machine 210 will generally be stored in mass storage system 268 and loaded into the internal memory of the computer 251 for rapid processing during use of the radiation therapy machine 211.

The radiation source 212 may be a linear accelerator excited in pulsed mode with the pulses in synchrony with the digital to analog converter of the data acquisition system 258 so as a set of views may be obtained during shutter opening and closing. If each projection of radiation at a given gantry angle, θ, during radiotherapy is one second, the pulse rate of linear accelerator may be two hundred times per second providing real-time motion study of movement of the leaves 230 based on the changing fluence exiting the leaf and entering the patient 217.

During operation of the radiation therapy system 211, the shutter system control 252 receives, from the computer 251, a treatment sinogram comprising a fluence profile for each gantry angle, θ. The treatment sinogram describes the intensity or fluence of each ray 228 of the radiation beam 214 that is desired for each gantry angle, θ, at a given position of the patient support table (not shown) as translated through the radiation beam 214.

Figure 3A:
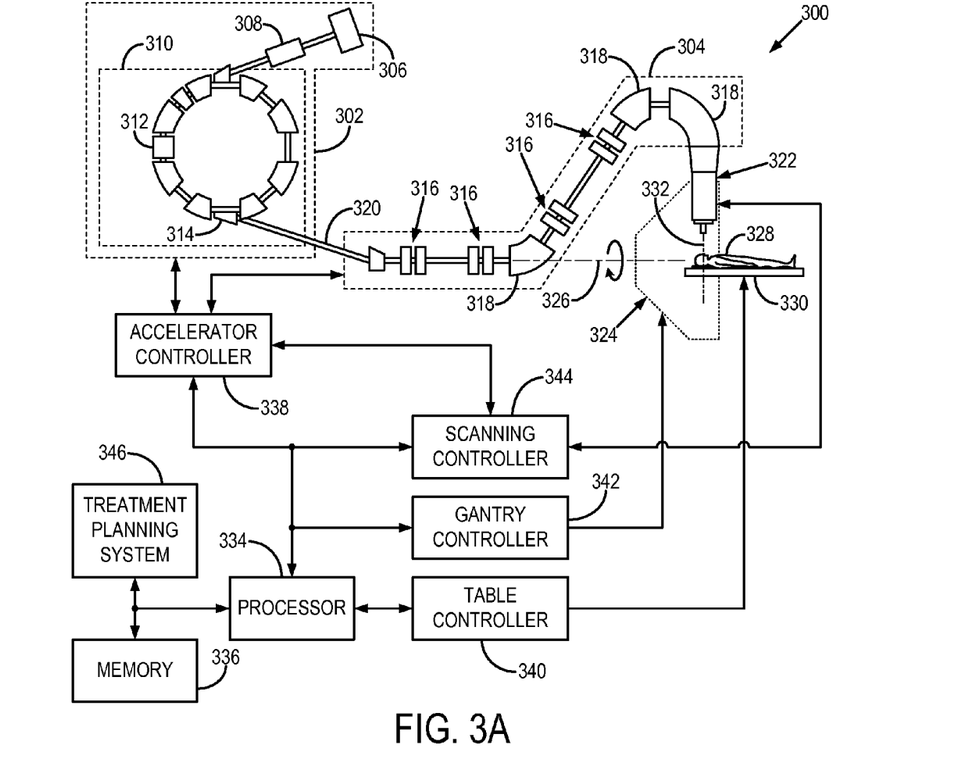
FIG. 3A is a block diagram of an exemplary hadron therapy system, such as a proton therapy system.
Figure 3B:
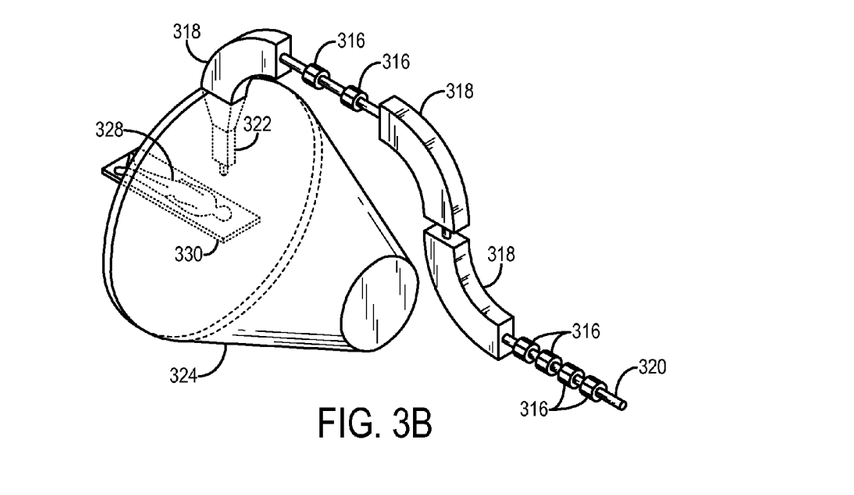
FIG. 3B is a perspective view of deflection optics coupled to a rotatable gantry, which both form a part of an exemplary hadron therapy system, such as the hadron therapy system of FIG. 3A.

Referring now to FIGS. 3A and 3B, an exemplary hadron therapy system 300, such as, for example, a proton beam therapy system, is illustrated. Exemplary hadrons for use with a hadron therapy system include protons, neutrons, and atoms or molecules containing such particles. For example, hadron therapy may include proton therapy, heavy ion therapy, and neutron therapy. An exemplary hadron therapy system 300 generally includes a charged particle generating system 302 and a beam transport system 304. By way of example, the charged particle generating system 302 may include a synchrotron; however, in other configurations the charged particle generating system 302 may include a cyclotron, or for some neutron therapy systems, the charged particle generating system 302 may include a linac configured to operate as a deuterium-tritium ("D-T") neutron generator. An exemplary proton beam treatment system is more fully disclosed in U.S. Pat. No. 4,870,287, which is hereby incorporated by reference in its entirety.

The charged particle beam generating unit 302 includes an ion source 306; an injector 308, such as a linac; and an accelerator 310, such as a synchrotron. The accelerator 310 includes at least one radio frequency ("RF") acceleration cavity 312. Exemplary RF acceleration cavities may include an RF applying electrode that is disposed on the circulating orbit of the accelerator 310 and an RF power source that is in electrical communication with the RF applying electrode by way of a switch.

Ions generated in the ion source 306, such as hydrogen ions (protons) or carbon ions, are accelerated by the injector 308 to form an ion beam that is injected into the accelerator 310. The accelerator 310 provides energy to the injected ion beam by way of the acceleration cavity 312, where RF energy is applied to the ion beam. In the case of a synchrotron, quadropole and dipole magnets are used to steer the ion beam about the accelerator 310 a number of times so that the ion beam repeatedly passes through the acceleration cavity 312. After the energy of the ion beam traveling in the accelerator 310 has reached a preselected, desired energy level, such as 100-200 mega-electron volts ("MeV"), the ion beam is extracted from the accelerator 310 through an extraction deflector 314. Extraction may occur by way of bumping, or kicking, the ion beam to an outer trajectory so that it passes through a septum, or by way of resonance extraction.

The beam transport system 304 includes a plurality of focusing magnets 316 and steering magnets 318. Exemplary focusing magnets 316 include quadropole magnets, and exemplary steering magnets 318 include dipole magnets. The focusing and steering magnets 316, 318 are used to contain the ion beam in an evacuated beam transport tube 320 and to deliver the ion beam to a beam delivery device 322 that is situated in a treatment room. The beam delivery device 322 is coupled to a rotatable gantry 324 so that the beam delivery device 322 may be rotated about an axis of rotation 326 to delivery therapeutic radiation to a patient 328 positioned on a patient table 330. The rotatable gantry 324 supports the beam delivery device 322 and deflection optics, including focusing and steering magnets 316, 318, that form a part of the beam transport system 304. These deflection optics rotate about the rotation axis 326 along with the beam delivery device 322. Rotation of the rotatable gantry 324 may be provided, for example, by a motor (not shown in FIGS. 3A and 3B). In some configurations, the accelerator 310 provides an ion beam to a plurality of beam delivery devices located in different treatment rooms. In such configurations, the beam transport system 304 may connect to a series of switchyards that may include an array of dipole bending magnets that deflect the ion beam to any one of a plurality of deflection optics that each lead to a respective beam delivery device in the respective treatment room.

The beam delivery device 322 is designed to deliver precise dose distributions to a target volume within a patient. In general, an exemplary beam delivery device 322 includes components that may either modify or monitor specific properties of an ion beam in accordance with a treatment plan. The beam delivery device 322 may, for example, include a device to spread or otherwise modify the ion beam position and profile, a dispersive element to modify the ion beam energy, and a plurality of beam sensors to monitor such properties. For example, scanning electromagnets may be used to scan the ion beam in orthogonal directions in a plane that is perpendicular to a beam axis 332.

The hadron therapy system 300 is controlled by a central controller that includes a processor 334 and a memory 336 in communication with the processor 334. An accelerator controller 338 is in communication with the processor 334 and is configured to control operational parameters of the charged particle generating system 302, including the accelerator 310, and the beam transport system 304. A table controller 340 is in communication with the processor 334 and is configured to control the position of the patient table 330. A gantry controller 342 is also in communication with the processor 334 and is configured to control the rotation of the rotatable gantry 324. A scanning controller 344 is also in communication with the processor and is configured to control the beam delivery device 322. The memory 336 may store a treatment plan prescribed by a treatment planning system 346 that is in communication with the processor 334 and the memory 336, in addition to control parameters to be delivered to the accelerator controller 338, the table controller 340, the gantry controller 342, and the scanning controller 344. The memory 336 may also store relevant patient information that may be beneficially utilized during a treatment session.

Before the ion beam is provided to the patient 328, the patient 328 is positioned so that the beam axis 332 intersects a treatment volume in accordance with a treatment plan prescribed by a treatment planning system 346 that is in communication with the processor 334. The patient 328 is positioned by way of moving the patient table 330 into the appropriate position. The patient table 330 position is controlled by the table controller 340, which receives instructions from the processor 334 to control the position of the patient table 330. The rotatable gantry 324 is then rotated to a position dictated by the treatment plan so that the ion beam will be provided to the appropriate treatment location in the patient 328. The rotatable gantry 324 is controlled by the gantry controller 342, which receives instructions from the processor 334 to rotate the rotatable gantry 324 to the appropriate position. As indicated above, the position of the ion beam within a plane perpendicular to the beam axis 332 may be changed by the beam delivery device 322. The beam delivery device 322 is instructed to change this scan position of the ion beam by the scanning controller 344, which receives instruction from the processor 334. For example, the scanning controller 344 may control scanning electromagnets located in the beam delivery device 322 to change the scan position of the ion beam.

In conventional radiation therapy a dose of 2 Grays ("Gy") is delivered at a dose rate of 4-6 Grays per minute ("Gy/min"). By reducing the effective dose rate and increasing the treatment time for each individual fraction, cellular repair processes can occur during irradiation. To take advantage of this phenomenon, pulsed reduced dose rate ("PRDR") was developed as a retreatment technique that delivers, for example, a series of 0.2 Gy pulses separated by 3 minute time intervals, creating an apparent dose rate of 0.0667 Gy/min.

It is well known that radiation dose rate has a significant impact on biological effect. It should be noted, however, that reduced dose rates typically result in a lower impact on malignant tissues, thereby resulting in less effective tumor control probability ("TCP"). Therefore, in order to maintain a clinically significant TCP, the radiation dose rate used in clinical external beam radiation therapy must remain within a general range of values. Dose rates at the lower end of this range of values, however, typically result in a reduced effect on normal tissue complication probability ("NTCP"), which is a desirable goal.

It is also well known that increasing the time during intrafraction irradiation of the planned target volume ("PTV") leads to diminished cell killing within in the PTV. For example, studies have shown that if fraction time in IMRT exceeds 10-15 minutes, the prescription dose delivered to the PTV needs to be increased in order to compensate for the reduction in cell killing due to the increased sublethal damage repair. If a treatment exceeds a certain length of time, that is, if the effective dose rate is diminished, there can be a significant loss of biological effect, but that loss of effectiveness is more pronounced for normal tissues than it is for malignant tissues. This phenomenon is described, for example, by J. F. Fowler, et al., in "Loss of Biological Effect in Prolonged Fraction Delivery," *Int. J. Radiat. Oncol. Biol. Phys.*, 2004; 59:242-249.

It has been observed in the clinic by many that normal tissues are more sensitive to alterations in radiation dose rate than tumors are, and this well-known observation has led to the present discovery. By employing a biologically motivated radiation beam distribution that is both spatially and temporally asymmetrical, NTCP can be substantially reduced while maintaining a clinically significant dose rate in the PTV. Indeed, NTCP can be lowered even further than achievable with standard step-and-shoot methods. In this manner, the same or increased prescribed dose is experienced by the PTV, but a lower NTCP is achieved in the healthy tissues and organs at risk ("OAR") surrounding the PTV.

Using the provided method, the sequence of radiation beams to be turned on and off during delivery of radiation to a patient is specifically designed to substantially reduced radiobiological effect on normal tissues, thereby diminishing the potential for long term injury. This in turn allows an increase in the radiation dose imparted to the malignant, or otherwise targeted, tissues in the PTV. In this manner, the efficacy of the treatment is increased without further detriment to adjacent healthy tissues. The means by which this is achieved is to decrease the effective dose rate of radiation to the selected normal tissues by spatiotemporally separating the radiation beams that irradiate these tissues.

By way of example, an overly simplified radiation treatment planning scenario is now presented to provide a clear example through which the present invention can be described. Following this example, a more detailed description of the method of the present invention is provided.

Figure 4:
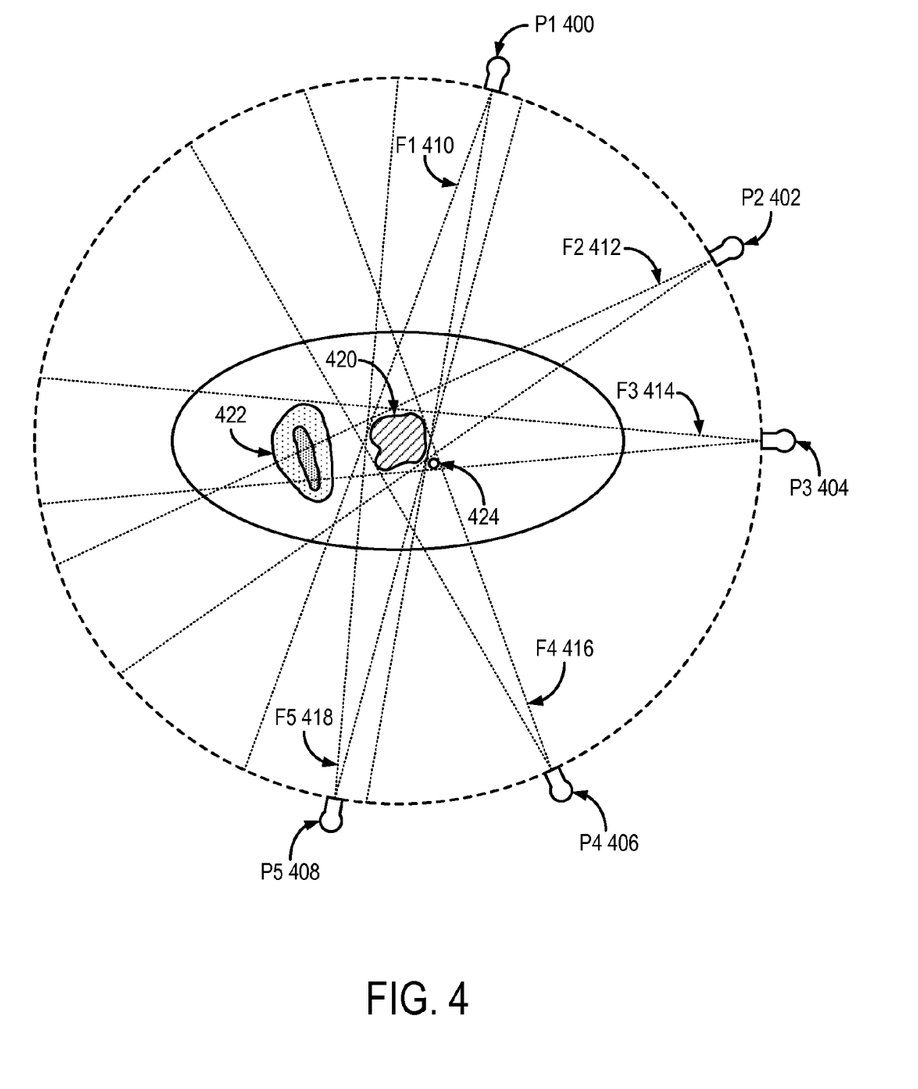
FIG. 4 is an illustrative example of a simplified radiation treatment plan.

Referring to FIG. 4, an exemplary radiation treatment includes moving the radiation source to five different gantry angles (P1 400, P2 402, P3 404, P4, 406, and P5, 408), thereby producing five different radiation beams, or "fields," at each of those respective gantry angles (F1 410, F2 412, F3 414, F4 416, and F5 418). These fields are all directed at a tumor 420 in a PTV, but three of the fields (F2 412, F3 414, and F4 416) also irradiate sensitive normal tissue structures such as a kidney 422 and spinal cord 424. In conventional treatment planning, the beams are turned on in no specific sequence, typically, in a left-to-right, clockwise, counterclockwise, or other simple sequence depending on technical efficiency. However, this is not the most effective manner for limiting the NTCP in the kidney 422 and spinal cord 424.

Instead, with the discovery that tumors are less sensitive than normal tissue to changes in dose rate, the present invention utilizes this discovery to design a more beneficial timing sequence to maximally separate, in time, the fields that irradiate the normal tissues (F2 412, F3 414, and F4 416). This temporal separation of radiation fields that irradiate normal structures significantly reduces the biological effect and thus reduces the chances of radiation-related toxicity in the normal tissues. This spatiotemporal patterning of dose distribution and dose rate is determined by taking into account the repair half-life and other radiobiological effect factors of the healthy tissue in the beam paths. Thus, in this simplified example, it is desired to design the treatment plan such that the dose rate to the tumor 420 is high, but the dose rate to the kidney 422 and spinal cord 424 are low.

In this manner, the radiation source would be moved to gantry angle P2 402 and the subject irradiated by radiation field F2 412 first, since it contains the tumor 420 and kidney 422, but not the spinal cord 424. Next, the radiation source would be rotated to P4 406 and the subject irradiated by radiation field F4 416 since it contains the tumor 420 and the spinal cord 424, but not the kidney 422. The determination to irradiate the subject with field F2 412 before field F4 416 is made in accordance with the repair half-life characteristics of the kidney 422 versus the spinal cord 424, which has a shorter repair half-life. After irradiating the subject with field F4 416, the radiation source is rotated to P5 408 and P1 400 sequentially since the radiation fields F5 418 and F1 400 corresponding to these gantry angles contain only the tumor 420. In this manner, the kidney 422 and spinal cord 424 are allowed to undergo cellular repair while the tumor 420 is further irradiated. This allows a high, clinically significant dose rate to be maintained in the tumor 420, while lowering the effective dose rate to the sensitive normal tissue structures. Lastly, the radiation source is rotated to gantry angle P3 404 and the subject irradiated with radiation field F3 414 since it contains the tumor 420, kidney 422, and spinal cord 424. By irradiating the subject along gantry angle P3 404 last, the treatment plan provides a substantially maximum amount of time in which the kidney 422 and spinal cord 424 are allowed to undergo cellular repair in accordance with their respective tissue repair characteristics, such as repair half-life. In this manner, a clinically effective dose rate is maintained in the tumor, while the dose rate, and thereby radiobiological effect, in surrounding healthy tissues is significantly reduced. Thus, an effective TCP is maintained while achieving lower NTCP than previously allowable.

Figure 5:
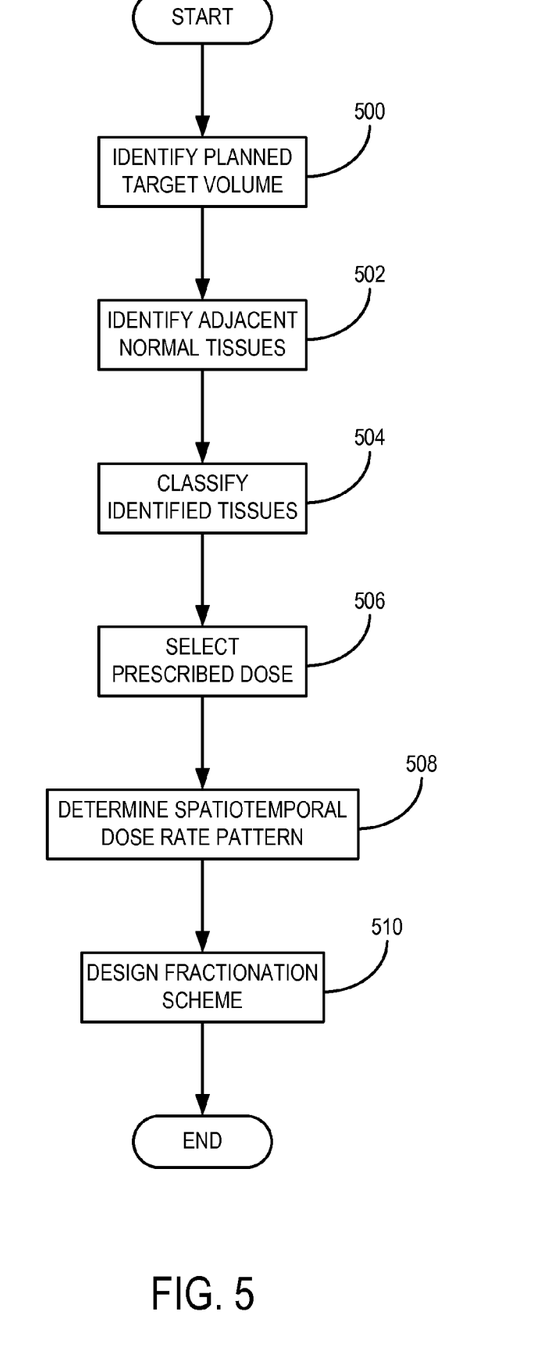
FIG. 5 is a flowchart setting forth the steps of an exemplary method for producing a biologically modulated radiation treatment plan in accordance with the present invention.

Referring now to FIG. 5, a flowchart setting forth the steps of an exemplary method for determining a biologically modulated radiation treatment plan in accordance with the present invention is illustrated. The method begins by identifying the planning target volume ("PTV") that contains the tumor or other target tissue to be treated, as indicated at step 500. Typically, this identification is made using an image of the subject that is acquired with the IGRT system; however, images of the subject that were previously acquired with other imaging systems can also be employed with the appropriate image registration to the treatment system. Next, the normal tissues and organs at risk that are adjacent to the PTV are identified from the same image of the subject used in step 500, as indicated at step 502. Following the identification of the adjacent normal tissues, these tissues are classified, as indicated at step 504. For example, an image segmentation is performed such that different tissues are appropriately segmented and classified according to their respective tissue types. An exemplary segmentation will identify those regions in an image of the subject that are associated with different tissue types such as kidney, heart, lung, liver, and spinal cord. Moreover, the different tissue types can be further classified as either healthy or diseased. In this manner, a segmented treatment image is produced in which each segment corresponds to a particular tissue type. Next, a prescribed dose that is to be imparted to the PTV is selected, as indicated at step 506.

The formulation of the radiation treatment plan then proceeds by designing the appropriate spatiotemporal dose rate pattern by which radiation is to be delivered to the subject in order to impart the prescribed dose to the PTV, as indicated at step 508. As discussed above, the spatiotemporal dose rate pattern is designed such that a substantially sustained dose rate is administered to the PTV while lower effective dose rates are administered to the adjacent normal tissues. Using the information regarding the location and classification of each tissue type surrounding the PTV that is obtained from the segmented treatment image, the desired spatiotemporal dose rate distribution is determined.

In any given clinical scenario, differing priorities will present themselves and these priorities may be factored into the selection process regarding to which organs the effective dose rate will be intentionally reduced. By way of example, assume that radiation therapy to a particular neck tumor would result in relatively high dose to the parotid salivary glands and the spinal cord. In this scenario, the actual total doses to each sensitive normal structure (spinal cord and parotid glands) is first predicted by a treatment planning computer algorithm. If a solution using the proposed mechanism presents itself that reduces dose rate to both of these sensitive structures, that option would be selected. If, however, the treatment plan identifies that dose rate cannot be reduced to both sensitive organs, then the organ that is more likely to experience injury from the treatment plan is selected for intentional dose rate reduction. For example, if the spinal cord dose were 42 Gy and the parotid gland dose were 30 Gy, the parotid gland would likely be selected as the organ to which dose rate is reduced. This selection is made since the spinal cord can typically tolerate up to 46 Gy, whereas the parotid glands can be injured by 25-30 Gy. In this case the designed spatiotemporal dose rate pattern would thereby reduce the parotid gland effective dose rate and, thus, protect it from injury while the spinal cord total dose would be under the normal tolerance and also be protected from injury without modifying effective dose rate. Another possible scenario might be if the spinal cord dose was 45 Gy and the parotid gland dose was over 30 Gy. Since injury to the spinal cord is a severe side effect, this organ would be chosen for effective dose rate reduction to avoid potentially devastating complications.

In another approach, a computerized treatment algorithm that includes factors such as total dose and daily fraction size, using, for example, the so-called linear-quadratic ("LQ") formalism, can be employed to calculate risk of injury from a conventional dose rate treatment. Such a program would then generate the optimized spatiotemporal dose rate pattern that would minimize risks of radiation injury in an automated fashion for any given clinical scenario. It is acknowledged that such algorithms would differ in their specifics for the various commercially available treatment planning systems that are currently in clinical use; however, the general concept of spatiotemporal modulation with the intent of effective dose rate reduction to minimize risk of injury could be universally applied.

After the spatiotemporal dose rate pattern is designed, the overall fractionation scheme for the treatment plan is determined, as indicated at step 510. The fractionation scheme describes the number and timing of different fractions of radiation treatment that are to be delivered to the subject in order to produce the prescribed dose in the PTV.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for controlling a radiation therapy system in order to deliver radiation to a planned target volume, the steps comprising:
    a) obtaining an image of a subject;
    b) identifying, in the obtained image of the subject, the planned target volume (PTV);
    c) identifying, in the obtained image of the subject, normal tissues adjacent the PTV;
    d) classifying each identified normal tissue adjacent the PTV;
    e) selecting a prescribed dose to be imparted to the PTV;
    f) determining, using the prescribed dose and information about a location and classification of each identified normal tissue and the identified PTV, a spatiotemporal dose rate distribution that maintains a selected dose rate to the PTV and a lower effective dose rate to the identified normal tissues, such that normal tissue complication probability (NTCP) is reduced, wherein step f) includes determining the spatiotemporal dose rate distribution by taking into account a repair half-life for each identified normal tissue such that the spatiotemporal dose rate distribution results in dose rates being adjusted in the identified normal tissues as a function of the repair half-life of each identified normal tissue; and
    g) directing the radiation therapy system to irradiate the PTV according to the determined spatiotemporal dose rate distribution.

2. The method as recited in claim 1 in which the determined spatiotemporal dose rate distribution identifies an order in which a radiation source that forms a part of the radiation therapy system is to be moved through each of a plurality of gantry angles.

3. The method as recited in claim 2 in which the determined spatiotemporal dose rate distribution identifies a duration of time in which the radiation source delivers radiation to the subject at each of the plurality of gantry angles.

4. The method as recited in claim 1 in which the radiation therapy system is at least one of an x-ray therapy system, an electron therapy system, a gamma ray therapy radiation system, and a hadron therapy system.

5. The method as recited in claim 4 in which the radiation therapy system is at least one of an image-guided x-ray therapy system, an image-guided electron therapy system, and an image-guided gamma ray therapy system.

6. The method as recited in claim 4 in which the radiation therapy system is a tomotherapy system.

7. The method as recited in claim 4 in which the hadron therapy system is at least one of a proton beam therapy system, a heavy ion beam therapy system, and a neutron beam therapy system.

8. The method as recited in claim 1 in which step f) includes determining the spatiotemporal dose rate distribution by taking into account radiobiological effect factors associated with each identified normal tissue such that the spatiotemporal dose rate distribution results in dose rates being reduced as a function of a radiosensitivity of each identified normal tissue.

9. The method as recited in claim 1 in which the spatiotemporal dose rate distribution determined in step f) results in reducing dose rate as the repair half-life for a given identified normal tissue increases.

10. A method for producing a radiation therapy treatment plan, the steps comprising:
    a) providing an image of a subject;
    b) identifying, in the provided image of the subject, a planned target volume (PTV) that is to receive treatment;
    c) identifying, in the provided image of the subject, normal tissues adjacent the PTV;
    d) classifying each identified normal tissue adjacent the PTV;
    e) selecting a prescribed dose to be imparted to the PTV; and
    f) determining, using the prescribed dose and information about a location and classification of each identified normal tissue and the identified PTV, a radiation therapy treatment plan that, when employed by a radiation therapy system, maintains a selected dose rate to the PTV and a lower effective dose rate to the identified normal tissues such that normal tissue complication probability (NTCP) is reduced, wherein step f) includes determining a spatiotemporal dose rate distribution by taking into account a repair half-life for each identified normal tissue such that the spatiotemporal dose rate distribution results in dose rates being adjusted in the identified normal tissues as a function of the repair half-life of each identified normal tissue.

11. The method as recited in claim 10 in which step c) includes segmenting the provided image.

12. The method as recited in claim 10 in which the spatiotemporal dose rate distribution determined in step f) defines an order in which a radiation source that forms a part of the radiation therapy system is to be moved through each of a plurality of treatment positions.

13. The method as recited in claim 12 in which each of the plurality of treatment positions define a position and an orientation of a radiation beam delivered by the radiation therapy system.

14. The method as recited in claim 12 in which the spatiotemporal dose rate distribution determined in step f) defines a duration of time during which the radiation therapy system delivers radiation to the subject at a given radiation treatment location.

15. The method as recited in claim 10 in which the spatiotemporal dose rate distribution determined in step f)

defines a duration of time during which the radiation therapy system delivers radiation to the subject at a given radiation treatment location.

16. The method as recited in claim 10 in which the spatiotemporal dose rate distribution determined in step f) results in reducing dose rate as the repair half-life for a given identified normal tissue increases.

* * * * *

UNITED STATES PATENT AND TRADEMARK OFFICE
CERTIFICATE OF CORRECTION

PATENT NO.         : 8,613,694 B2                                            Page 1 of 1
APPLICATION NO.    : 13/010047
DATED              : December 24, 2013
INVENTOR(S)        : James Sherman Welsh It is certified that error appears in the above-identified patent and that said Letters Patent is hereby corrected as shown below:

On the Title Page, Item (76), "Walsh", should be --Welsh--.

Signed and Sealed this
Twenty-second Day of April, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,613,694 B2 | Page 1 of 1 |
| APPLICATION NO. | : 13/010047 | |
| DATED | : December 24, 2013 | |
| INVENTOR(S) | : James Sherman Welsh | |

It is certified that error appears in the above-identified patent and that said Letters Patent is hereby corrected as shown below:

On the Title Page, Item (12), delete "Walsh" and insert --Welsh--.

On the Title Page, Item (76), "Walsh", should be --Welsh--.

This certificate supersedes the Certificate of Correction issued April 22, 2014.

Signed and Sealed this
Thirteenth Day of May, 2014

Michelle K. Lee
*Deputy Director of the United States Patent and Trademark Office*